United States Patent [19]
Babiak et al.

[11] Patent Number: 5,536,869
[45] Date of Patent: Jul. 16, 1996

[54] PROCESS FOR THE PREPARATION OF ETHYL 3S-[4-[[4-(AMINOIMINOMETHYL)PHENYL] AMINO]-1,4-DIOXOBUTYL]AMINO]-4-PENTYNOATE

[75] Inventors: Kevin A. Babiak, Evanston, Ill.; Srinivasan Babu, San Diego, Calif.; James R. Behling, Lindenhurst, Ill.; Mark L. Boys, Buffalo Grove, Ill.; Kimberly J. Cain-Janicki, Sleepy Hallow, Ill.; Wendel W. Doubleday, Twin Lakes, Wis.; Payman Farid, Vernon Hills, Ill.; Timothy J. Hagen, Gurnee, Ill.; E. Ann Hallinan, Evanston, Ill.; Donald W. Hansen, Jr., Skokie, Ill.; Donald E. Korte, Mundelein, Ill.; Kathleen T. McLaughlin, Arlington Heights, Ill.; John R. Medich, Gurnee, Ill.; Sean T. Nugent, Grayslake, Ill.; Vlasdislav Orlovski, Buffalo Grove, Ill.; Jung M. Park, Glenview, Ill.; Karen B. Peterson, Vernon Hills, Ill.; Daniel R. Pilipauskas, Glenview, Ill.; Barnett S. Pitzele, Skokie, Ill.; Sofya Tsymbalov, Skokie, Ill.; Glenn L. Stahl, Buffalo Grove, Ill.

[73] Assignee: G. D. Searle & Co., Chicago, Ill.

[21] Appl. No.: 502,054

[22] Filed: Jul. 14, 1995

[51] Int. Cl.$^6$ ................................................. C07C 229/24
[52] U.S. Cl. ................................................................. 560/35
[58] Field of Search ................................................. 560/35

[56] References Cited

U.S. PATENT DOCUMENTS

| | | | |
|---|---|---|---|
| 5,239,113 | 8/1993 | Bovy et al. | 562/440 |
| 5,344,957 | 9/1994 | Bovy et al. | 560/35 |

OTHER PUBLICATIONS

D. Hua et al. "Synthesis of 4–Substituted 2–Azetidinones", Tetrahedron Letters, vol. 26, No. 5, pp. 547–550 (1985), Great Britain.

T. Kametani "Synthesis of Carbapenem Antibiotics", Heterocycles, vol. 17, pp. 463–506, (1982), Tokyo, Japan.

D. Cole "Recent Stereoselective Synthetic Approaches to β–Amino Acids", Tetrahedron vol. 50, No. 32, pp. 9517–9582 (1994), Great Britain.

J. Rico, et al. "A Highly Stereoselective Michael Addition To An α,β–Unsaturated Ester As The Crucial Step In the Synthesis Of A Novel β–Amino Acid–Containing Fibrinogen Receptor Antagonist", J. Org. Chem, 58, pp. 7948–7951 (1993), Washington, D.C., U.S.A.

E. Juaristi, et al. "Enantioselective Synthesis of β–Amino Acids", Aldrichimica Acta, vol. 27, No. 1 (1994), Milwaukee, WI, U.S.A.

K. Hattori, et al. "Highly Selective And Operationally Simple Synthesis of Enantiomerically Pure β–Amino Esters Via Double Stereodifferentiation", J. Am. Chem. Soc., 115, pp. 1151–1152 (1993), Washington, D.C., U.S.A.

G. Iwasaki, et al. "Further Studies On the Stereochemistry Of Metal Enolate–Imine Condensation Reactions", Tetrahedron Let., vol. 28, No. 28, pp. 3257–3260 (1987), Great Britain.

K. Hattori, et al. "A Novel Stereocontrolled Synthesis of 3–(1'–Hydroxyethyl)–2–Azetidinone", Synlett (3) pp. 239–240 (1993), Stuttgart, Germany.

*Primary Examiner*—Gary Geist
*Assistant Examiner*—Joseph M. Conrad, III
*Attorney, Agent, or Firm*—Joy Ann Serauskas; Roger A. Williams

[57] ABSTRACT

The present invention relates to a novel process for the preparation of ethyl 3S-[[4-[[4-(aminoiminomethyl)phenyl] amino]-1,4-dioxobutyl]amino]-4-pentynoate and pharmaceutically acceptable acid addition salt thereof which comprises treating (trimethylsilyl)acetylene sequentially with n-butyllithium and 4-formylmorpholine followed by acid hydrolysis to give 3-(trimethylsilyl)-2-propynal; treating 3-(trimethylsilyl)-2-propynal with lithium bis(trimethylsilyl)amide to give in situ N,3-bis(trimethylsilyl)-2-propyn-1-imine; condensation of N,3-bis(trimethylsilyl)-2-propyn-1-imine with lithium t-butyl acetate to give (±)1,1-dimethylethyl 3-amino-5-(trimethylsilyl)-4-pentynoate; treating (±)1,1-dimethylethyl 3-amino-5-(trimethylsilyl)-4-pentynoate- with p-toluenesulfonic acid to give (±)1,1-dimethylethyl 3-amino-5-(trimethylsilyl)-4-pentynoate, mono p-toluenesulfonic acid salt, treatment of resulting salt with ethanol in the presence of p-toluenesulfonic acid to give (±)ethyl 3-amino-5-(trimethylsilyl)-4-pentynoate; desilylation of (±)ethyl 3-amino-5-(trimethylsilyl)-4-pentynoate to give in situ (±)ethyl 3-amino-4-pentynoate; resolution of (±)ethyl 3-amino-4-pentynoate using (R)-(−)-mandelic acid and treatment of the resolved product with gaseous hydrochloric acid to give ethyl 3S-amino-4-pentynoate, monohydrochloride; coupling the ethyl 3S-amino-4-pentynoate, monohydrochloride to 4-[[4-(aminoiminomethyl)phenyl] amino]-4-oxobutanoic acid, monohydrochloride in the presence of isobutyl chloroformate and N-methylmorpholine to give ethyl 3S-[[4-[[4-(aminoiminomethyl)phenyl]amino]-1, 4-dioxobutyl]amino]-4-pentynoate, monohydrochloride.

1 Claim, No Drawings

PROCESS FOR THE PREPARATION OF ETHYL 3S-[4-[[4-(AMINOIMINOMETHYL)PHENYL]AMINO]-1,4-DIOXOBUTYL]AMINO]-4-PENTYNOATE

BACKGROUND OF THE INVENTION

The present invention relates to a novel process for the preparation of ethyl 3S-[[4-[[4-(aminoiminomethyl)phenyl]amino]-1,4-dioxobutyl]amino]-4-pentynoate having the following structural formula

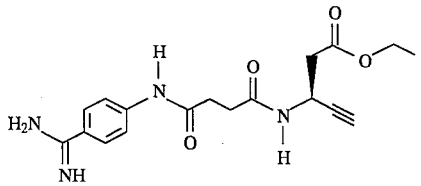

and the pharmaceutically acceptable acid addition salt thereof which comprises treating (trimethylsilyl) acetylene sequentially with n-butyllithium and 4-formylmorpholine in the presence of an aprotic solvent followed by acid hydrolysis to give 3-(trimethylsilyl)- 2-propynal; treating 3-(trimethylsilyl)- 2-propynal with lithium bis(trimethylsilyl)amide in the presence of an aprotic solvent to give N,3-bis(trimethylsilyl)-2-propyn-1-imine in situ; condensation of N,3-bis(trimethylsilyl)- 2-propyn-1-imine with lithium t-butyl acetate followed by hydrolytic cleavage to give (±)1,1-dimethylethyl 3-amino- 5-(trimethylsilyl)-4-pentynoate; treating (±)1,1-dimethylethyl 3-amino-5-(trimethylsilyl)-4-pentynoate with p-toluenesulfonic acid in the presence of aprotic solvents to give (±)1,1-dimethylethyl 3-amino-5-(trimethylsilyl)- 4-pentynoate, mono p-toluenesulfonic acid salt; treatment of the resulting salt with ethanol in the presence of p-toluenesulfonic acid, followed by neutralization to give (±)ethyl 3-amino-5-(trimethylsilyl)- 4-pentynoate; desilylation of (±)ethyl 3-amino-5-(trimethylsilyl)-4-pentynoate in the presence of a catalytic amount of base and an alkanol solvent to give in situ (±)ethyl 3-amino-4-pentynoate; resolution of (±)ethyl 3-amino-4-pentynoate using (R)-(−)-mandelic acid and treatment of the resolved product with gaseous hydrochloric acid to give ethyl 3S-amino-4-pentynoate, monohydrochloride; coupling the ethyl 3S-amino-4-pentynoate, monohydrochloride to 4-[[4-(aminoiminomethyl)phenyl]amino]-4-oxobutanoic acid, monohydrochloride in the presence of isobutyl chloroformate and N-methylmorpholine to give ethyl 3S-[[4-[[4-(aminoiminomethyl)phenyl]amino]-1,4-dioxobutyl]amino]-4-pentynoate, monohydrochloride.

The 4-[[4-(aminoiminomethyl)phenyl]amino]-4-oxobutanoic acid, monohydrochloride intermediate is prepared by treating commercially available 4-aminobenzamidine dihydrochloride with succinic anhydride and pyridine in the presence of an aprotic solvent.

The process of the present invention is useful for preparing ethyl 3S-[[4-[[4-(aminoiminomethyl)phenyl]amino]-1,4-dioxobutyl]amino]-4-pentynoate which is described in U.S. Pat. No. 5,344,957.

Ethyl 3S-[[4-[[4-(aminoiminomethyl)phenyl]amino]-1,4-dioxobutyl]amino]-4-pentynoate is the orally active prodrug of 3S-[[4-[[4-(aminoiminomethyl)phenyl]amino]- 1,4-dioxobutyl]amino]-4-pentynoic acid. The acid form is an active platelet aggregation inhibitor. A complete discussion of ethyl 3S-[[4-[[4-(aminoiminomethyl)phenyl]amino]- 1,4-dioxobutyl]amino]- 4-pentynoate and 3S-[[4-[[4-(aminoiminomethyl)-phenyl]amino]- 1,4-dioxobutyl]amino]-4-pentynoic acid usefulness as a platelet aggregation inhibitor is presented in the U.S. Pat. No. 5,344,957 patent.

U.S. Pat. No. 5,344,957 discloses a process for preparing ethyl 3S 3-[[4-[[4-(aminoiminomethyl)phenyl]amino]- 1,4-dioxobutyl]amino]-4-pentynoate having the following formula

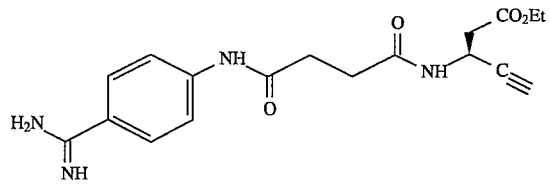

This process is described as follows: 4-Aminobenzamidine di-HCl (25 g, 120 mmol), which is commercially available, particularly from Aldrich, was added to dry DMF (100 ml). To this solution dry pyridine (100 ml) and succinic anhydride (12 g, 120 mmol) followed by dimethylaminopyridine (DMAP 1.5 g 0.012 mmol) were added. The product precipitated after heating for ½ h at 100° C. The product was filtered, washed with water, acetonitrile and ether. The light solid was suspended in dioxane, 4N HCl in dioxane (100 ml) was added and the suspension was stirred for 1 h, filtered and dried in a desiccator to give 28 g, 88% of 4-[[4-(aminoiminomethyl)phenyl]-amino]-4-oxobutanoic acid as a white yellow solid which decomposes between 270° C. and 290° C.

4-[[4-(Aminoiminomethyl)phenyl]amino]-4-oxobutanoic acid hydrochloride was added to dry DMF (35 ml) followed by N-methylmorpholine (0.39 g, 1 eq.) and isobutyl chloroformate (0.53 g, 3.9 mmol) at 25° C. The mixture was stirred for 5 min. (S)-ethyl 3-amino-4-pentynoate was added followed by diisopropylethylamine and a catalytic amount of dimethylaminopyridine. After 1 hour, the solvent was removed under reduced pressure and the product was purified by reverse phase chromatography to give (3S)-ethyl 3-[[4-[[4-(aminoiminomethyl)phenyl]amino]- 1,4-dioxobutyl]amino]-4-pentynoate.

The (S)ethyl 3-amino-4-pentynoate intermediate which is described above was prepared according to the procedures disclosed in Method 3 of Scheme V of the "957" patent. Similar reactions are also disclosed by D. H. Hua and A. Verma, Tetrahedron Lett. 547–550 (1985) and T. Kametani, Heterocycles Vol. 17 463 (1982). These references are also disclosed in the "957" patent.

SUMMARY OF THE INVENTION

The present invention relates to a process for the preparation of ethyl 3S-[[4-[[4-(aminoiminomethyl)phenyl]amino]- 1,4-dioxobutyl]amino]-4-pentynoate having the following formula:

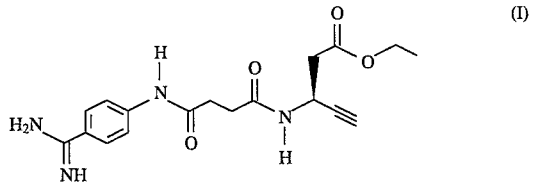

and the pharmaceutically acceptable salt thereof which comprises:

(a) treating (trimethylsilyl)acetylene sequentially with n-butyllithium and 4-formylmorpholine in the presence of an aprotic solvent followed by acid hydrolysis to give 3-(trimethylsilyl)-2-propynal;

(b) treating 3-(trimethylsilyl)-2-propynal, the product of step a, with lithium bis(trimethylsilyl)amide in the presence of an aprotic solvent to give N,3-bis(trimethylsilyl)-2-propyn- 1-imine in situ, treating N,3-bis(trimethylsilyl)-2-propyn- 1-imine with lithium t-butyl acetate followed by hydrolytic cleavage to give (±)1,1-dimethylethyl 3-amino-5-(trimethylsilyl)- 4-pentynoate;

(c) treating (±)1,1-dimethylethyl 3-amino-5-(trimethylsilyl)- 4-pentynoate, the product of step b, with p-toluenesulfonic acid in the presence of aprotic solvents to give (±)1,1-dimethylethyl 3-amino-5-(trimethylsilyl)-4-pentynoate, mono p-toluenesulfonic acid salt, treating the resulting salt with ethanol in the presence of p-toluenesulfonic acid, followed by neutralization to give (±)ethyl 3-amino-5-(trimethylsilyl)- 4-pentynoate;

(d) treating (±)ethyl 3-amino-5-(trimethylsilyl)-4-pentynoate, the product of step c, with a catalytic amount of base in the presence of an alkanol solvent followed by a catalytic amount of acid to give the desilylated (±)ethyl 3-amino-4-pentynoate in situ, treating (±)ethyl 3-amino-4-pentynoate with (R)-(−)-mandelic acid in the presence of aprotic solvents to give ethyl 3S-amino-4-pentynoate compounded with αR-hydroxybenzeneacetic acid;

(e) treating 4-aminobenzamidine dihydrochloride with succinic anhydride and pyridine in the presence of an aprotic solvent to give 4-[[4-(aminoiminomethyl)phenyl]amino]- 4-oxobutanoic acid, monohydrochloride;

(f) treating ethyl 3S-amino-4-pentynoate compounded with αR-hydroxybenzeneacetic acid, the product of step d, with gaseous hydrochloric acid in the presence of an aprotic solvent to give ethyl 3S-amino- 4-pentynoate, monohydrochloride; and (g) treating 4-[[4-(aminoiminomethyl)phenyl]amino]-4-oxobutanoic acid, monohydrochloride, the product of step e, with isobutyl chloroformate and N-methylmorpholine in the presence of an aprotic solvent followed by ethyl 3S-amino-4-pentynoate, monohydrochloride, the product of step f, with N-methylmorpholine to give ethyl 3S-[[4-[[4-(aminoiminomethyl)phenyl]amino]-1,4-dioxobutyl]amino]- 4-pentynoate, monohydrochloride with the understanding that when a pharmaceutically acceptable acid addition salt other than hydrochloride is desired the ethyl 3S-amino- 4-pentynoate compounded with αR-hydroxybenzeneacetic acid, the product of step d, is treated with the appropriate acid corresponding to the desired salt and with the further understanding that the final salt of step e is identical to the final salt of step f.

The present invention also relates to a process for preparing ethyl 3S-amino-4-pentynoate monohydrochloride having the following formula

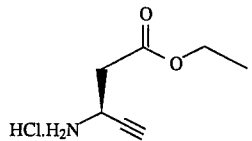

which comprises:

(a) treating (trimethylsilyl)acetylene sequentially with n-butyllithium and 4-formylmorpholine in the presence of an aprotic solvent followed by acid hydrolysis to give 3-(trimethylsilyl)-2-propynal;

(b) treating 3-(trimethylsilyl)-2-propynal, the product of step a, with lithium bis(trimethylsilyl)amide in the presence of an aprotic solvent to give N,3-bis(trimethylsilyl)-2-propyn- 1-imine in situ, treating N,3-bis(trimethylsilyl)- 2-propyn-1-imine with lithium t-butyl acetate followed by hydrolytic cleavage to give (±)1,1-dimethylethyl 3-amino-5-(trimethylsilyl)- 4-pentynoate;

(c) treating (±)1,1-dimethylethyl 3-amino-5-(trimethylsilyl)- 4-pentynoate, the product of step b, with p-toluenesulfonic acid in the presence of aprotic solvents to give (±)1,1-dimethylethyl 3-amino-5-(trimethylsilyl)-4-pentynoate, mono p-toluenesulfonic acid salt, treating the resulting salt with ethanol in the presence of p-toluenesulfonic acid, followed by neutralization to give (±)ethyl 3-amino-5-(trimethylsilyl)- 4-pentynoate; and (d) treating (±)ethyl 3-amino-5-(trimethylsilyl)-4-pentynoate, the product of step c, with a catalytic amount of base in the presence of alkanol solvent followed by a catalytic amount of acid to give the desilylated (±)ethyl 3-amino-4-pentynoate in situ, treating (±)ethyl 3-amino-4-pentynoate with (R)-(−)-mandelic acid in the presence of aprotic solvents to give ethyl 3S-amino-4-pentynoate compounded with αR-hydroxybenzeneacetic acid; and (e) treating ethyl 3S-amino-4-pentynoate compounded with αR-hydroxybenzeneacetic acid, the product of step d, with gaseous hydrochloric acid in the presence of an aprotic solvent to give ethyl 3S-amino- 4-pentynoate, monohydrochloride; with the understanding that when a pharmaceutically acceptable acid addition salt other than hydrochloride is desired the ethyl 3S-amino-4-pentynoate compounded with αR-hydroxybenzene acetic acid, the product of step d, is treated with the appropriate acid corresponding to the desired salt.

SCHEME A

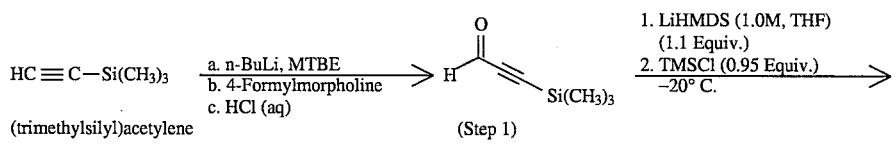

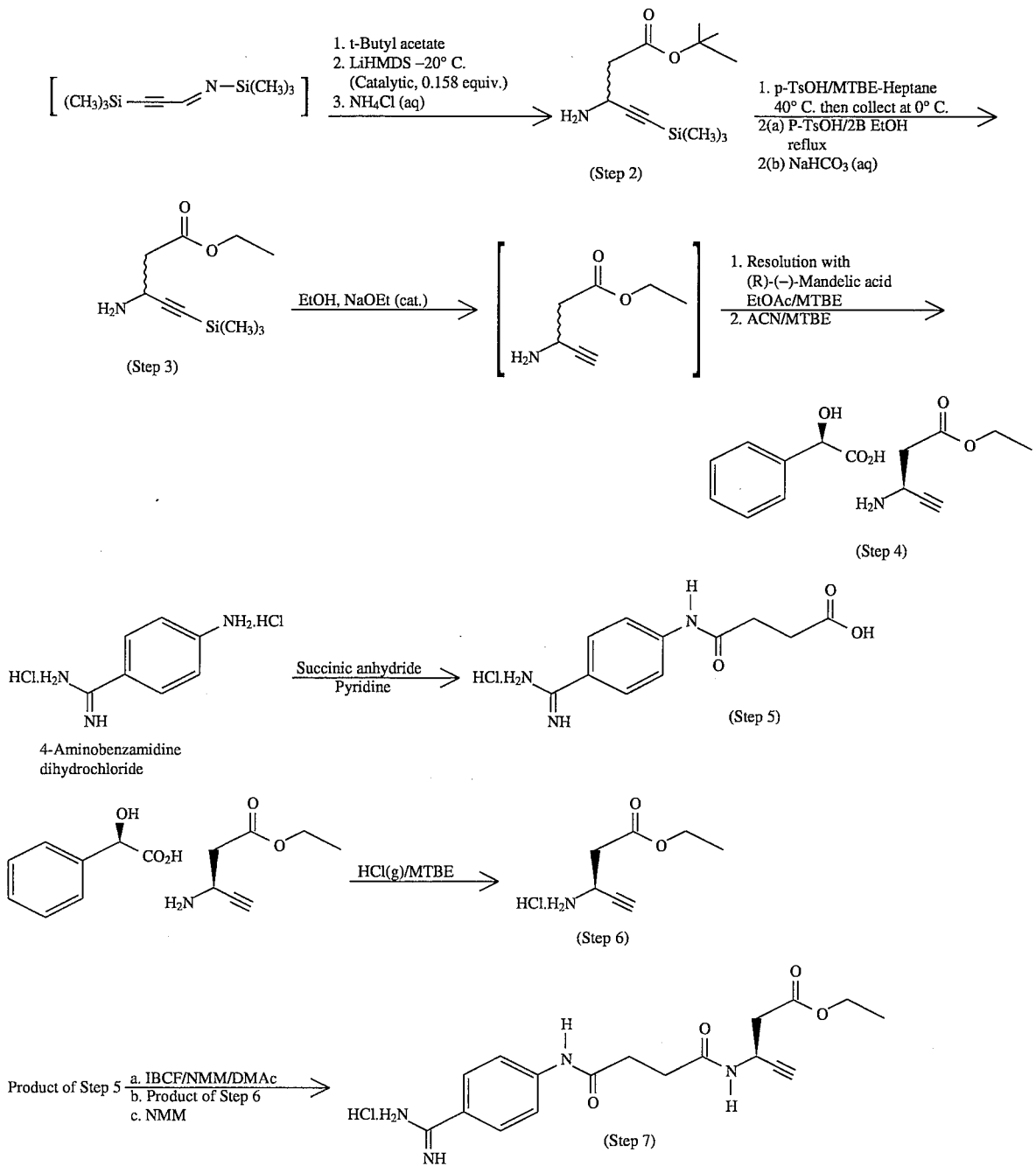
The aforementioned chemical names have the following structural formulas:
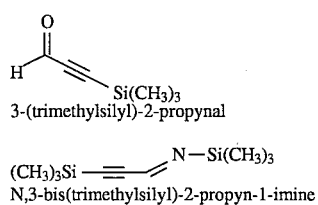
3-(trimethylsilyl)-2-propynal
N,3-bis(trimethylsilyl)-2-propyn-1-imine
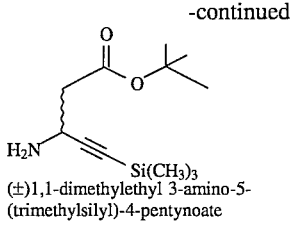
(±)1,1-dimethylethyl 3-amino-5-(trimethylsilyl)-4-pentynoate 5,536,869

7
-continued

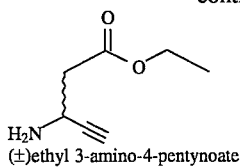
(±)ethyl 3-amino-4-pentynoate

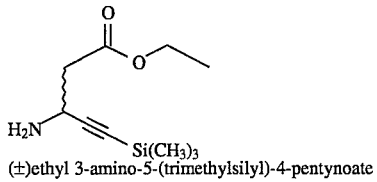
(±)ethyl 3-amino-5-(trimethylsilyl)-4-pentynoate

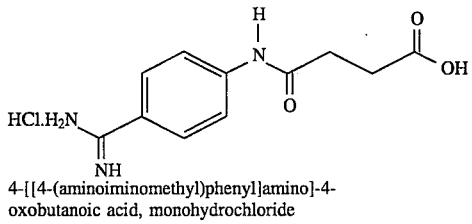
4-[[4-(aminoiminomethyl)phenyl]amino]-4-oxobutanoic acid, monohydrochloride

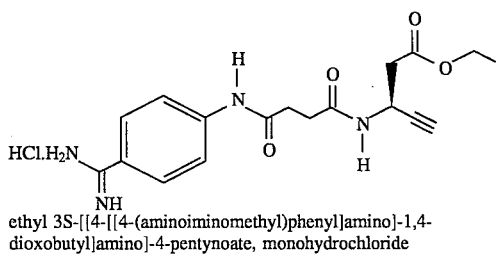
ethyl 3S-[[4-[[4-(aminoiminomethyl)phenyl]amino]-1,4-dioxobutyl]amino]-4-pentynoate, monohydrochloride

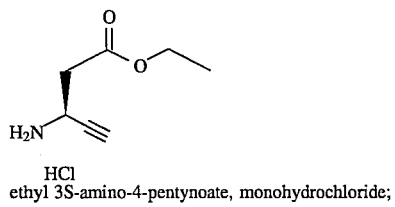
ethyl 3S-amino-4-pentynoate, monohydrochloride;

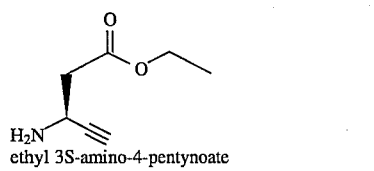
ethyl 3S-amino-4-pentynoate

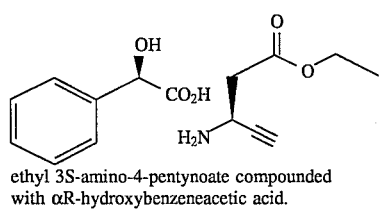
ethyl 3S-amino-4-pentynoate compounded with αR-hydroxybenzeneacetic acid.

As used herein the term "pharmaceutically acceptable acid addition salt" refers to a salt prepared by contacting a compound of formula I, with an acid whose anion is generally considered suitable for human consumption. Examples of pharmacologically acceptable salts include the hydrochloride, hydrobromide, hydroiodide, sulfate, phosphate, acetate, propionate, lactate, maleate, malate, succinate, and tartrate and citrate salts.

8
DETAILED DESCRIPTION OF THE INVENTION

The starting material for the process of this invention—(trimethylsilyl)acetylene—is commercially available. The process of the present invention is outlined in Scheme A and is described as follows:

Step 1 of Scheme A

The formylation step (step 1) of Scheme A is carried out at a temperature ranging from −45° to +5° C. with −10° C. being preferred using n-butyllithium in hexanes in the presence of an aprotic solvent and (trimethylsilyl) acetylene as the protected alkyne. To this reaction mixture with stirring at a temperature ranging from −15° to 5° C. is added 4-formylmorpholine. The resulting reaction mixture is allowed to stir for 2 h at a temperature ranging from 0° to 25° C., cooled to a temperature ranging from −15° to 0° C. and then added to an aqueous solution of HCl. This step yields 3-(trimethylsilyl)-2-propynal which is isolated from the reaction mixture and used in the next step. Suitable aprotic solvents are exemplified by tetrahydrofuran, dioxane, ethyl acetate and lower alkyl ethers which do not react with n-butyllithium such as methyl t-butyl ether (MTBE) with methyl t-butyl ether being preferred.

Step 2 of Scheme A

Lithium bis(trimethylsilyl)amide is placed in a reaction vessel to which 3-(trimethylsilyl)-2-propynal of step 1 is added in an aprotic solvent. During the addition of 3-(trimethylsilyl)-2-propynal the pot temperature should be maintained between −40° to −20° C. to ensure stability of the intermediate imine. To the resulting solution is added trimethylsilyl chloride and the resulting mixture stirred at a temperature ranging from −40° to −20° C. for 1 hour. This reaction step yields N,3-bis(trimethylsilyl)-2-propyn-1-imine which is not isolated from the vessel but is confirmed by GC. To the reaction vessel is now added t-butyl acetate and a catalytic amount of lithium bis(trimethylsilyl)amide. The reaction mixture is allowed to stir for 2 h at a temperature ranging from −40° to −20° C. to give (±)1,1-dimethylethyl 3-amino-5-(trimethylsilyl)-4-pentynoate which is isolated after an aqueous ammonium chloride quench and used in the next step. In order to insure complete cleavage of the nitrogen-silicon bond the stir time for this phase should not be less than 30 minutes.

Step 3 of Scheme A

The p-toluenesulfonic acid salt of (±)1,1-dimethylethyl 3-amino-5-(trimethylsilyl)-4-pentynoate is prepared by treating p-toluenesulfonic acid with (±)1,1-dimethylethyl 3-amino-5-(trimethylsilyl)-4-pentynoate, the product of step 2, in the presence of MTBE/heptane. The resulting reaction mixture is then heated to 55°–60° C. for one hour, cooled, filtered and dried to give (±) 1,1,-dimethylethyl 3-amino-5-(trimethylsilyl)-4-pentynoate, mono p-toluenesulfonic acid salt. The (±)1,1-dimethylethyl 3-amino-5-(trimethylsilyl)-4-pentynoate mono p-toluenesulfonic acid salt is treated with ethanol in the presence an organic acid or an inorganic acid at reflux temperature. The reaction mixture is then cooled to ambient temperature, concentrated and treated with methyl t-butyl ether and a suitable aqueous base to give ethyl 3-amino- 5-(trimethylsilyl)-4-pentynoate. Suitable inorganic acid agents are exemplified by sulfuric acid and hydrochloric acid and suitable organic acid agents are exemplified by camphorsulfonic acid and p-toluenesulfonic acid with p-toluenesulfonic acid being preferred. Suitable aqueous bases are exemplified by sodium bicarbonate, sodium carbonate, sodium hydroxide with sodium bicarbonate being preferred. Other alkanol solvents such as methanol, isopropanol, butanol and pentanol would also be suitable for the practice of this invention. However, it is to be understood that the use of a different alkanol solvent would give a different ester i.e. use of methanol for ethanol would give the corresponding methyl ester.

Step 4 of Scheme A (±) Ethyl 3-amino-5-(trimethylsilyl)-4-pentynoate the product of step 3 is desilylated in the presence of a catalytic amount of base and an alkanol solvent. Suitable bases are exemplified by potassium tert-butoxide, sodium hydroxide, sodium ethoxide and sodium carbonate with sodium ethoxide being preferred. The basic reaction is neutralized with an inorganic or organic acid to give an alkanol solution of ethyl 3-amino-4-pentynoate which is used in the next step without isolation. Suitable inorganic acid agents are exemplified by hydrochloric acid, sulfuric acid and phosphoric acid with suitable organic agents being exemplified by p-toluenesulfonic acid, acetic acid, camphorsulfonic acid and cationic exchange resin with sulfuric acid being preferred. Suitable alkanol solvents are exemplified by methanol, ethanol, isopropanol and butanol with ethanol being preferred. Resolution of (±) ethyl 3-amino-5-(trimethylsily)- 4-pentynoate using R-(−)-mandelic acid in the presence of aprotic solvents gives ethyl 3S-amino-4-pentynoate compounded with αR-hydroxybenzeneacetic acid. Suitable aprotic solvents are exemplified by tetrahydrofuran, dioxane, ethyl acetate, and lower alkyl ethers such as methyl t-butyl ether with a mixture of ethyl acetate and methyl t-butyl ether being preferred.

Step 5 of Scheme A

Treatment of 4-aminobenzamidine dihydrochloride, which is commercially available, with succinic anhydride in the presence of N,N-dimethylformamide and pyridine gives 4-[[4-(aminoiminomethyl)phenyl]amino]-4-oxobutanoic acid, as a mixture of the zwitterion and the hydrochloride. The product is isolated from the crude reaction mixture by the addition of conc HCl in acetone followed by additional acetone. Filtration and treatment with aqueous HCl gives 4-[[4-(aminoiminomethyl)phenyl]-amino]- 4-oxobutanoic, monohydrochloride.

Step 6 of Scheme A

Treatment of ethyl 3S-amino-4-pentynoate compounded with αR-hydroxybenzeneacetic acid (the product of step 4) with gaseous hydrochloric acid in the presence of an aprotic solvent gives ethyl 3S-amino-4-pentynoate, monohydrochloride. Suitable aprotic solvents are exemplified by tetrahydrofuran, dioxane, ethyl acetate and lower alkyl ethers such as methyl t-butyl ether (MTBE) with methyl t-butyl ether being preferred.

Step 7 of Scheme A

4-[[4-Aminoiminomethyl)phenyl]amino]-4-oxobutanoic acid, monohydrochloride, the product of Step 5, is coupled with ethyl 3S-amino-4-pentynoate hydrochloride, the product of Step 6, in presence of isobutyl chloroformate and N-methylmorpholine to give ethyl 3S-[[4-[[4-(aminoiminomethyl)phenyl]amino]- 1,4-dioxobutyl]amino]-4-pentynoate, monohydrochloride. The reaction temperature for this step should be maintained between −15° to 0° C. The reaction sequence is the following:

(a) the product of step 5 which is 4-[[4-aminoiminomethyl)phenyl]amino]- 4-oxobutanoic, hydrochloride in N,N-dimethylacetamide (DMAc) is cooled to −15° to −10° C.;

(b) to the cooled reaction mixture is added isobutyl chloroformate (IBCF) followed by N-methylmorpholine (NMM);

(c) to this reaction mixture is now added ethyl 3S-amino-4-pentynoate hydrochloride in DMAc, followed by the addition of N-methylmorpholine; and (d) the resulting reaction mixture is warmed to ambient temperature and the desired product isolated. Suitable solvents in place of the preferred N,N-dimethylacetamide (DMAc) would be N,N-dimethylformamide (DMF) and N-methylpyrrolidinone (NMP).

The present invention provides a safe, convenient and cost effective manufacturing process for the production of ethyl 3S-[[4-[[4-(aminoiminomethyl)phenyl]amino]-1,4 dioxobutyl]amino-4-pentynoate, monohydrochloride. Its safety is demonstrated by the elimination of potentially hazardous solvents and reagents. The subject process in step 5 of Scheme A utilizes aqueous HCl/acetone mixture in place of the ether and dioxane of the "957" patent. Its convenience is demonstrated by the synthetic route comprising a limited number of steps. Its cost effectiveness is demonstrated by the final product being produced in high yield and high quality.

A major difference between the process described in the "957" patent for the preparation ethyl 3S-[[4-[[4-(aminoiminomethyl)phenyl]amino]- 1,4-dioxobutyl]amino]-4-pentynoate, monohydrochloride and the process of the present invention is in the use of a different solvent, a lower reaction temperature and the absence of 4-dimethylaminopyridine during the coupling reaction as well as the elimination of chromatography and lyophilization. In "957" patent, the reaction is conducted in DMF at 25° C. for both the activation and coupling steps. In addition, 4-dimethylaminopyridine is added during the coupling phase.

The following examples are provided to illustrate the present invention and are not intended to limit the scope thereof. All temperatures expressed are in degrees centigrade. Within the foregoing synthetic description and examples which follow, abbreviations have the following meanings:

ACN=acetonitrile
DMF=N,N dimethylformamide
DMSO=dimethylsulfoxide
g=gram
EtOH=ethanol
Ether=diethylether
min=minute
h=hour
mL=milliliter
mol=mole
mmol=mmole
NMM=N-methylmorpholine
RPHPLC=Reverse Phase High Pressure Liquid Chromatography
LiHMDS=lithium bis(trimethylsilyl)amide
THF=tetrahydrofuran
TMSCl=trimethylsilyl chloride NaOEt=sodium ethoxide
p-TsOH=p-toluenesulfonic acid
MTBE=methyl t-butyl ether
IBCF=isobutyl chloroformate
DMAc=N,N-dimethylacetamide Infrared (IR) spectra are recorded on a Perkin-Elmer® 681 spectrophotometer. Nuclear magnetic resonance (NMR) spectra are obtained on a Varian® VXR-400 spectrometer using tetramethylsilane as internal standard. Elemental analyses are obtained using a Control Equipment Model 240XA Elemental Analyzer (C, H and N) and a Mettler potentiometric titration system (total Cl and Cl). Differential scanning calorimetry (DSC) analyses are obtained using a DuPont® Model 9900 thermal analysis system.

Chemical reactions are monitored by gas chromatography (GC), High Pressure Liquid Chromatography (HPLC) or thin layer chromatography (TLC) on Macherey-Nagel® SIL G-25 UV$_{254}$ silica gel plates. Chemical intermediates are analyzed by GC or high performance liquid chromatography (HPLC). Qualitative estimates of purity are based upon integration of the area under the peaks in the GC or HPLC chromatograms.

| GC Method A | |
|---|---|
| Column | Rtx-5 (5% Diphenyl, 95% dimethyl polysiloxane; 30 m × 0.53 mm i.d., 5-micron film thickness) |
| Oven Temp. | 35° C. (2 min) to 250° C. (2 min) at 10° C./min |
| Injector Temp. | 180° C. |
| Detector Temp. | 250° C. |
| Detection | FID |
| Column Flow Rate | Helium at 4 mL/min |
| Split Mode | Splitless |
| Injection Volume | 1 mcL |
| Sample | 5 mg/mL in methyl t-butyl ether |
| Concentration | 20–30 mg/mL in methyl t-butyl ether |

| GC Method B | |
|---|---|
| Column | DB-17 (50% Diphenyl, 50% methyl silicone; 15 m × 0.53 mm i.d., 1-micron film thickness) |
| Oven Temp. | 35° C. (5 min) to 250° C. (5 min) at 10° C./min |
| Injector Temp. | 250° C. |
| Detector Temp. | 250° C. |
| Detection | FID |
| Column Flow Rate | Helium at 20 mL/min |
| Split Mode | Splitless |
| Injection Volume | 1 mcL |
| Sample | 3 mg/mL |
| Concentration | 1 mg/mL |
| Derivatization | N-Methyl-N-(trimethylsilyl)-trifluoroacetamide (MSTFA) |

| GC Method C | |
|---|---|
| Column | HP-1 (Methyl silicone; 15 m × 0.53 mm i.d., 2.65-micron film thickness) |
| Oven Temp. | 50° C. (5 min) to 250° C. (10 min) at 15° C./min |
| Injector Temp. | 240° C. |
| Detector Temp. | 260° C. |
| Detection | FID |
| Column Flow Rate | Helium at 20 mL/min |
| Split Mode | Splitless |
| Injection Volume | 0.5 mcL |
| Sample | 5 mg/mL in methyl t-butyl ether |
| Concentration | 3 mg/mL in methyl t-butyl ether |

| HPLC Method A | |
|---|---|
| Column | Chiralcel OD (25 cm × 4.6 mm) |
| Column Temp. | Ambient |
| Mobile Phase | Hexane/Isopropanol, 85/15 (v/v) |
| Flow Rate | 2 mL/min |
| Sample Concentration | 1.6 mg/mL |
| Injection Volume | 10 mcL |
| Detection | UV at 230 nm |

| HPLC Method B | |
|---|---|
| Column | YMC AQ-303 (25 cm × 4.6 mm) |
| Column Temp. | Ambient |
| Mobile Phase | Acetonitrile/1% Triethylammonium phosphate buffer, pH 3, 5/95 (v/v) |
| Flow Rate | 1 mL/min |
| Sample | 1 mg/mL in mobile phase |
| Concentration | 0.5 mg/mL in mobile phase |
| Injection Volume | 10 mcL |
| Detection | UV at 210 nm |

EXAMPLE 1

Preparation of 3-(trimethylsilyl)-2-propynal

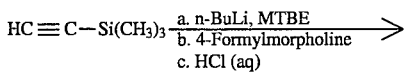

To a 1 L, three-necked round bottomed flask equipped with a mechanical stirrer, a pressure-equalized dropping funnel, a temperature probe and a nitrogen inlet was charged 59 mL of (trimethylsilyl)acetylene and 210 mL of methyl t-butyl ether (MTBE) at ambient temperature affording a pale yellow homogeneous solution. This homogeneous solution was mechanically stirred while being cooled with an acetone/dry ice bath to at least −15° C. The dropping funnel was charged with 245 mL of n-butyllithium (n-BuLi) (1.6M; hexanes) which was added as fast as possible to the cold solution while maintaining the batch temperature below 0° C. The resulting homogeneous solution was stirred at −15° C. for 10 to 15 min. A new, clean dropping funnel was charged with 40 mL of 4-formylmorpholine which was added as fast as possible to the cold solution while maintaining the batch temperature below 15° C. The resulting homogeneous solution was then warmed to ambient temperature (ca. 22° C.) by removing the cooling bath. After stirring for approximately 2 h, during which time the reaction mixture became heterogeneous, the reaction mixture was cooled in an acetone/dry ice bath to −15° C. While the reaction mixture was being cooled again, 340 mL of a pre-made 10% aq HCl solution was charged to a 1 L erlenmeyer flask and magnetically stirred at ambient temperature (ca. 22° C.). Once the organic solution reached −15° C., the heterogeneous solution was charged as quickly as possible to 300 mL of the 10% aq HCl solution and the resulting mixture was magnetically stirred for at least 15 min. During this time, the heterogeneous organic layer changes to a transparent yellow one. An in-process check (IPC) was performed on an aliquot using Gas Chromatrography (GC) Method A to confirm the presence of the desired product. The quenched mixture was charged to a separatory funnel. The layers were separated and the organic layer was washed with 300 mL of 20% aq. NaCl and the layers were separated. The solvent was removed by reduced pressure resulting in 45.7 g of the title compound (molar yield = 91%) as a 60–95 wt % solution. The concentration of the desired product is determined by an acceptance test using GC Method B. An analytical sample may be obtained by reduced pressure distillation.

A sample of purified title compound analyzed as follows: $^1$H NMR (CDCl$_3$) δ8.90 ppm (s, 1H, CHO), 0.00 (s, 9H, TMS) ppm; $^{13}$C NMR (CDCl$_3$) δ176.5, 102.8, 102.2, 1.0 ppm; IR: 2155 (C≡C), 1667 (CHO) CM$^{-1}$; Anal calc'd for C$_6$H$_{10}$OSi: C, 57.09; H, 7.98; Found: C, 56.86; H, 8.25.

EXAMPLE 2

Preparation of (+)1,1-dimethylethyl 3 amino-5-(trimethylsilyl)-4-pentynoate

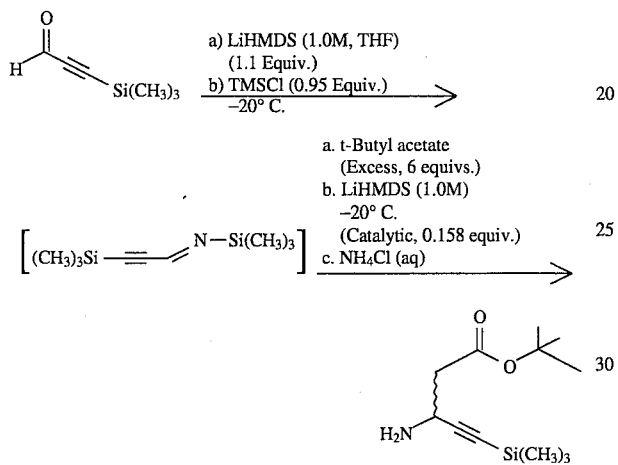

To a 500 mL, 3-neck round bottom flask equipped with a mechanical stirrer and under a blanket of nitrogen was charged 110 mL of lithium bis(trimethylsilyl)amide (1.0M solution in THF) while maintaining the internal temperature at −20° C. using an isopropanol/dry ice bath. Once the desired temperature was attained, 20.14 g of 3-(trimethylsilyl)- 2-propynal (a 62.7% solution in MTBE) was added to the reaction flask over 2 h. Upon completing the addition, the reaction mixture was stirred for 10 min at −20° C. followed by the addition of 10.3 g of trimethyl silyl chloride over a period of 20 min while maintaining the batch temperature at −20° C. Upon completing the addition the reaction mixture was stirred for 10 min at which time 69.7 g of t-butyl acetate was added to the reaction mixture over 15 min while maintaining the batch temperature at −20° C. The reaction mixture was stirred for 10 min at −20° C. at which time 19.2 mL of lithium bis(trimethylsilyl)amide (1.0M solution in THF) was added over a period of 40 min while maintaining the batch temperature at −20° C. An in-process check was performed on an aliquot using GC Method C to ensure that the area % of the desired product was >55%. The reaction mixture was added to an ammonium chloride solution (prepared by adding 5.0 g of ammonium chloride in 25 mL of water) and the mixture was allowed to reach ambient temperature with stirring (25° C.). The mixture was stirred at ambient temperature (25° C.) for 1 h. The mixture was transferred to a separatory funnel and the phases were separated. An in-process check was performed using GC Method C to determine the presence of desired product. This material was used without further purification. The solvent from the organic phase was removed under reduced pressure to give 34.5 g of the title compound as a brown oil (49.52 wt %, a molar yield of 70.7%).

An analytical sample may be obtained by crystallization of the p-toluenesulfonic acid salt from heptane/MTBE. Liberation of the free amine by treatment with aqueous potassium carbonate and extraction into an organic solvent such as MTBE gives (following removal of solvent) pure (±)1,1-dimethylethyl 3 amino-5-(trimethylsilyl)- 4-pentynoate. Alternatively, the free amine may be purified by distillation under vacuum.

A sample of purified (±)1,1-dimethylethyl 3-amino-5-(trimethylsilyl)- 4-pentynoate analyzed as follows: $^1$H NMR (CDCl$_3$, 400 MHz) δ3.96(1H, dd), 2.60–2.47 (2H, m), 1.65 (2H, s, —NH$_2$), 1.45 (9H, s), 0.15 (9H, s). $^{13}$C NMR (CDCl$_3$, 125 MHz) δ170.05, 107.96, 86.60, 80.85, 43.87, 41.02, 28.05 (3C), −0.13 (3C). Anal. calcd for C$_{12}$N$_{23}$NO$_2$Si: C, 59.70; H, 9.60: N, 5.80. Found: C, 59.85; H, 9.67; N, 5.74.

EXAMPLE 3

Preparation of (±)ethyl 3-amino-5-(trimethylsilyl)-4-pentynoate

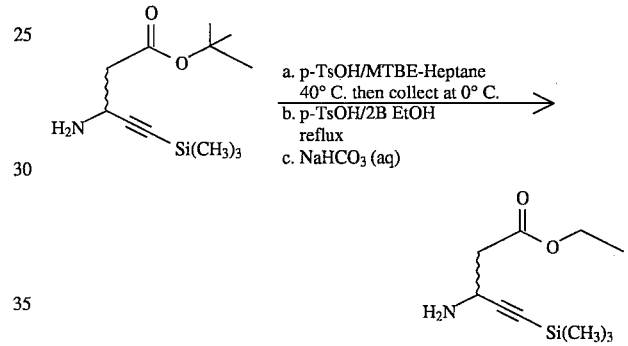

A mixture containing 80 g of p-toluenesulfonic acid, 116 mL of MTBE, 829 mL of heptane and 280 g of (±)1,1-dimethylethyl 3-amino-5-(trimethylsilyl)-4-pentynoate (35.7 wt % solution in THF) was heated to 55°–60° C. for 1 h. The homogeneous solution was cooled to 40° C. over 1 h and then to 5° C. over 1 h at which time the resulting heterogeneous mixture was held at 5° C. for 1 h. The mixture was vacuum filtered and the cake was washed with 2×160 mL of heptane and dried on the filter with a nitrogen flow to give 142 g of (±)1,1-dimethylethyl 3-amino- 5-(trimethylsilyl)-4-pentynoate, mono p-toluenesulfonic acid salt (83% molar yield) which was used without further purification.

A solution containing 142 g of (±)1,1-dimethylethyl 3-amino-5-(trimethylsilyl)-4-pentynoate, mono p-toluenesulfonic acid salt and 20 g of p-toluenesulfonic acid in 260 mL of 2B ethanol was stirred and heated to reflux. After refluxing for 4 h, the reaction mixture was cooled to ambient temperature and concentrated on a rotary evaporator. With vigorous agitation, 344 mL of MTBE was added to the distillation residue followed by 949 g of 5% aq NaHCO$_3$ with considerable gas evolution observed during the latter. The mixture was stirred for 30 min and the layers were separated. The aqueous layer was extracted with 140 mL of MTBE; the layers were separated and the organic phases were combined. The combined organic phases were washed with 206 g of 7% aq NaHCO$_3$ and allowed to stand for 15 min before the layers were separated. The organic layer was dried over MgSO$_4$, filtered, and concentrated on the rotary evaporator to afford 60.4 g of the title compound (83% molar yield) as a yellow oil: $^1$H NMR (CDCl$_3$) δ4.19 (q, 2H), 4.0 (m, 1H), 2.6 (m, 1H), 1.65 (s, 1H), 1.28 (t, 3H), 0.15 (s, 9H) ppm; $^{13}$C NMR: 170.7, 107.7, 86.8, 60.5, 42.7, 40.8, 14.1, −0.2 ppm; IR (neat): 3315–3383 cm$^{-1}$ (NH), 2960–2978 cm$^{-1}$ (CH), 2105–2166 cm$^{-1}$ (C≡C), 1735 cm$^{-1}$ (C=O); Anal. Calcd for C$_{10}$H$_{19}$NO$_2$Si: C, 56.30; H, 8.98; N, 6.56; Found: C, 56.67; H, 8.77; N, 6.27.

EXAMPLE 4

Preparation of ethyl 3S-amino-4-pentynoate monohydrochloride

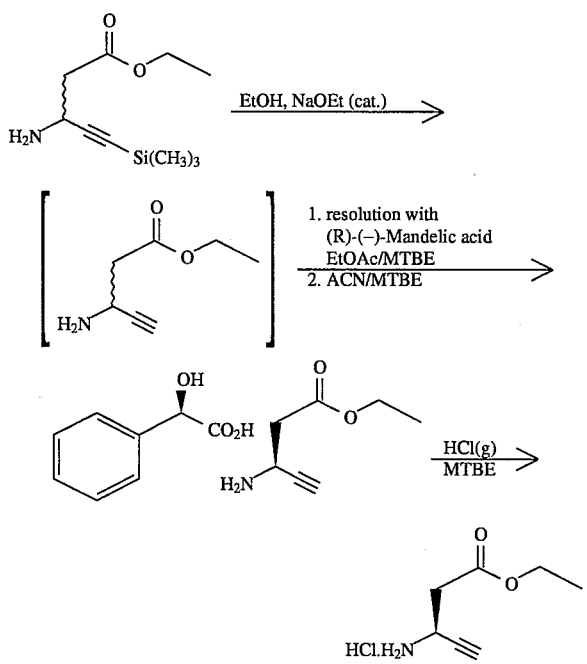

Desilylation of (±)ethyl 3-amino-5-(trimethylsilyl)-4-pentynoate

To a 3 L round bottomed flask equipped with a magnetic stirrer, a pressure-equalized addition funnel, a thermocouple and nitrogen inlet was added 305.4 g of (±)ethyl 3-amino-5-(trimethylsilyl)-4-pentynoate and 800 mL of 2B ethanol. To the resulting homogeneous solution was added dropwise 90.0 g of a 21 wt % solution of sodium ethoxide in ethanol. The reaction was stirred at 25° C. for 30 min. To the basic solution was added 14.1 g (7.8 mL) of concentrated sulfuric acid and the resulting reaction mixture was stirred for 30 min.

Mandelic Acid Salt Formation and Isolation

To the above solution was added 213.3 g of (R)-(−)-mandelic acid all at once and the mixture was stirred for 60 min at 25° C. The bulk of the solvent was removed by distillation under reduced pressure maintaining the batch temperature below 35° C. The resulting residue was suspended in 500 mL of ethyl acetate and the solvent was once again removed by distillation under reduced pressure to remove remaining ethanol. The ethyl acetate treatment was repeated two more times. The resulting milky residue was suspended in 1.6 L of ethyl acetate which was transferred to a jacketed 2 L non-baffled vessel. To this heterogeneous solution was added 450 mL of MTBE and the resulting mixture was warmed to 30° C. resulting in a transparent brown solution. The warmed solution was cooled to 0° C. over 3 h. The crystallization mixture was held at 0° C. for 4 h. The solids were isolated by filtration, washed with 2×200 mL of ethyl acetate:MTBE (30:70 v/v) and dried at 30°–40° C. affording 124 g of a beige solid (30% molar yield). The chirality of the title product was determined to be 92% S by HPLC Method A.

Recrystallization

To 122 g of the above solids was added 1.3 L of acetonitrile and the mixture was stirred 1 h at ambient temperature. To the homogeneous solution was added 60 g of Solka floc™ filter aid and the resulting heterogeneous mixture was filtered using house vacuum. The filter cake was washed with 2×100 mL of acetonitrile. The filtrate was concentrated using a rotary evaporator to a final concentration of 5 L of acetonitrile per kg of crude ethyl 3S-amino-4-pentynoate compounded with αR-hydroxybenzene acetic acid. The concentration was monitored by measuring the weight remaining in the distillation vessel. To the concentrated solution was added 0.6 L of MTBE (5 L/kg) and the heterogeneous mixture was heated to 35°–50° C. to dissolve the solids. The solution was cooled to 0° C. over 3 h. The crystallization was held for at least 4 h at 0° C. The solids were isolated by vacuum filtration, washed with 3×50 mL of MTBE and dried in a vacuum oven at 30°–40° C. to afford 89.4 g ethyl 3S-amino-4-pentynoate compounded with αR-hydroxybenzeneacetic acid (21% molar yield from (±)ethyl 3-amino-5-(trimethylsilyl)-4-pentynoate). The chirality of the title product was determined to be 99.6% S by HPLC Method A. DSC endotherm at 102.17° C.; IR: (KBr) 3297 cm$^{-1}$ (N—H), 2132 cm$^{-1}$ (C≡C), 1744 cm$^{-1}$ (C=O), 1563 cm$^{-1}$ (C=O); $^1$H NMR: (CDCl$_3$) δ7.42–7.2 (m, 5H), 6.0 (br.s, 4H), 5.0 (s, 1H), 4.15 (q, 2H), 4.03 (m, 1H), 2.67 (m, 2H), 2.32 (d, 1H), 1.25 (t, 3H) ppm; $^{13}$C NMR (CDCl$_3$): δ178.4, 170.0, 140.6, 128.3, 127.6, 126.7, 79.9, 74.5, 74.1, 61.3, 39.2, 38.5, 14.1 ppm; Anal. calcd for C$_{15}$H$_{19}$NO$_5$: C, 61.42; H, 6.53; N, 4.78 Found: C, 61.43; H, 6.56; N, 4.63.

Hydrochloride Salt Formation

A suspension of 18.0 g of ethyl 3S-amino-4-pentynoate compounded with αR-hydroxybenzeneacetic acid and 178 mL of MTBE were stirred at ambient temperature for 15 min at which time the suspension was cooled to 10° C. in an ice/water bath. Gaseous HCl (5.2 g) was slowly bubbled into the reaction mixture while maintaining the batch temperature at 10° C. The ice bath was removed allowing the reaction to warm to ambient temperature. After 4.5 h, the reaction mixture was filtered, the solids were washed with MTBE and air dried overnight to afford 9.9 g of the title compound (94% molar yield):DSC:endotherm at 133.67° C., $^1$H NMR (C$_2$D$_5$OD) δ5.21 (br.s, 3H), 4.45 (m, 1H), 4.2 (q, 2H), 3.68 (d, 1H), 3.0 (dd, 1H), 2.85 (dd, 1H), 1.29 (t, 3H) ppm; $^{13}$C NMR (C$_2$D$_5$OD): δ169.6, 78.2, 77.9, 62.1, 38.3, 37.5, 13.9, ppm; Anal. Calcd for: C$_7$H$_{12}$NO$_2$Cl: C, 47.33; H, 6.81; N, 7.89; Cl, 19.96; Found: C, 47.42; H, 6.72; N, 7.70; Cl, 19.64.

EXAMPLE 5

Preparation of 4-[[4-(aminoiminomethyl)phenyl]amino]-4-oxobutanoic acid, monohydrochloride

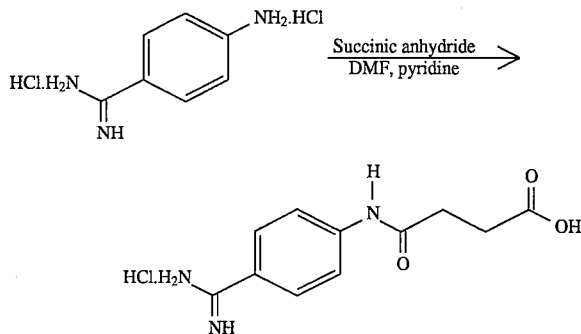

A mixture of 2.2 g of 4-aminobenzamidine dihydrochloride, 1.1 g of succinic anhydride and 10 mL of DMF was stirred at ambient temperature for 15 min at which time 0.83 mL of pyridine was added all at once. The resulting heterogeneous mixture was warmed to 100° C. and maintained at 100° C. for 1.5 h. The disappearance of starting material was monitored by an in-process check using HPLC Method B. After cooling to 0° C., a solution of 8 wt % concentrated HCl in acetone was added slowly while maintaining the temperature at 0° C. After the addition of additional acetone, the resulting milky suspension was stirred for 30 min and the solids were collected by vacuum filtration. The solids were then washed twice each with aq 0.5M HCl followed by acetone and were dried in a vacuum oven at 30°–40° C. to afford 2.4 g (88% molar yield) of the title compound. Acceptance testing was performed on the product using HPLC Method B to determine the presence of the title product. $\lambda_{max}$ (CH$_3$OH) 281 nm; (0.1% H$_3$PO$_4$ in water) 203,270 nm; IR (KBr): 1736 (C=O), 1674 (C—N, C=N), 1599 (C=N) cm$^{-1}$; DSC endotherms at 167° C. and 275° C.; $^1$H NMR: (d$_6$-DMSO) δ12.15 (s, 1H), 10.55 (s, 1H), 9.23 (s, 2H), 9.0 (s, 2H), 7.81 (s, 4H), 3.31 (s, 3H), 2.62 (m, 2H), 2.55 (m, 2H) ppm; $^{13}$C NMR: δ173.6, 171.0, 164.8, 144.3, 129.1, 121.2, 118.3, 31.2, 28.6 ppm; Anal calcd for C$_{11}$H$_{14}$N$_3$O$_3$Cl.0.25 H$_2$O: C, 47.83, H, 5.29; N, 15.21; Cl, 12.84; Found: C, 47.68; H, 5.02; N, 15.23; Cl, 12.92.

EXAMPLE 6

Preparation of ethyl 3S-[[4-[[4-aminoiminomethyl)phenyl]amino]-1,4-dioxobutyl]amino]-4-pentynoate, monohydrochloride

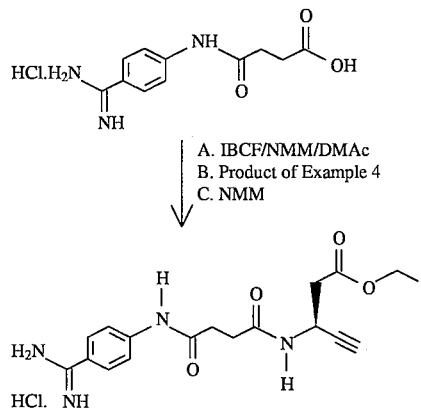

A mixture containing 0.95 g of 4-[[4-(aminoiminomethyl)phenyl]amino]- 4-oxobutanoic acid, monohydrochloride in 20 mL of DMAc was stirred at ambient temperature until homogeneous at which time the solution was cooled to −10° C. To this cold solution was added 0.5 mL of isobutyl chloroformate followed by 0.43 mL of N-methylmorpholine while maintaining the batch temperature below 0° C. After stirring this solution at −10° C. for 1 h a solution of 0.63 g of ethyl 3S-amino-4-pentynoate monohydrochloride in 5 mL of DMAc was added all at once followed by 0.38 mL of N-methylmorpholine while maintaining the batch temperature below 0° C. The temperature of the reaction mixture was adjusted to −5° C. and stirred at this temperature for 3 h at which time the reaction mixture was warmed to ambient temperature and the solvent was removed under reduced pressure. To the distillation residue was added 5 mL of 5% aq NaCl solution and the resulting aqueous solution was stirred for 30 min at ambient temperature. This solution was added dropwise over 30 min to 20 mL of a 30% aq NaCl solution and the resulting milky suspension was stirred at ambient temperature for 1 h. The suspension was vacuum filtered and the solids were washed with 2×25 mL of 25% aq NaCl at which time they were dried in a vacuum oven at 50° C. until a Karl Fisher analysis (see U.S. Pharmacopeia XXIII, 1995, p. 1841) indicated that less than or equal to 1 wt % of water was present. At this time the solids containing the title product, sodium chloride and reaction impurities were suspended in DMF (2.5 ml/g), stirred for 1 h and filtered to remove the NaCl. The filtrate was added to acetone (10 times the DMF volume), stirred for 2 h, filtered and washed with additional acetone. The solids were suspended in acetone (10 times DMF volume), refluxed for 1 h, cooled to ambient temperature, filtered, washed with acetone (same as DMF volume) and dried in a vacuum oven overnight at 50° C. to afford 0.9 g of the title compound as an off-white powder (65% molar yield): [α](DMSO) −35.0 at 589 nm, −131.7 at 365 nm; DSC: endotherms at 202.8° C. and 213.7° C.; IR: 1672$^1$ (C—N, C=N), 1721 (C=O), 2118 (C≡C), 3352–3240 (NH, CN) cm$^{-1}$; $^1$H NMR: (d$_6$-DMSO) δ10.50 (s, 1H), 9.11 (br.s, 4H), 8.47 (d, 1H), 7.80 (m, 4H), 4.87 (q.d, 1H), 4.07 (q, 2H), 3.22 (d, 1H), 2.58–2.70 (m, 4H), 2.36–2.50 (m, 2H), 1.18 (t, 3H) ppm; $^{13}$C NMR: δ171.1, 170.3, 169.1, 164.7, 144.2, 129.0, 121.1, 118.2, 82.8, 73.2, 60.1, 40.0, 37.0, 31.4, 29.6, 13.9 ppm; Anal. Calcd for C$_{18}$H$_{23}$N$_4$O$_4$Cl: C, 54.75; H, 5.87; N, 14.19; Cl, 8.98; Found: C, 54.39; H, 5.90; N, 14.09; Cl, 9.24.

What we claim is:

1. A process for the preparation of ethyl 3S[[4-[[4-(aminoiminomethyl)phenyl]amino]- 1,4-dioxobutyl]-amino]-4-pentynoate having the following formula

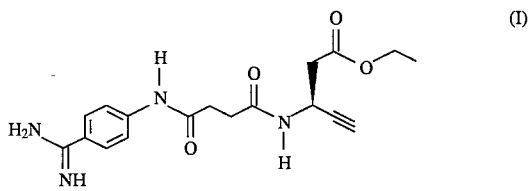

and the pharmaceutically acceptable acid addition salt thereof which comprises:

(a) treating (trimethylsilyl)acetylene sequentially with n-butyllithium and 4-formylmorpholine in the presence of an aprotic solvent followed by acid hydrolysis to give 3-(trimethylsilyl)-2-propynal;

(b) treating 3-(trimethylsilyl)-2-propynal, the product of step a, with lithium bis(trimethylsilyl)amide in the presence of an aprotic solvent to give N,3-bis(trimethylsilyl)- 2-propyn-1-imine in situ, treating N,3-bis(trimethylsilyl)-2-propyn-1-imine with lithium t-butyl acetate followed by hydrolytic cleavage to give (±)1,1-dimethylethyl 3-amino-5-(trimethylsilyl)- 4-pentynoate;

(c) treating (±)1,1-dimethylethyl 3-amino-5-(trimethylsilyl)- 4-pentynoate, the product of step b, with p-toluenesulfonic acid in the presence of aprotic solvents to give (±)1,1-dimethylethyl 3-amino- 5-(trimethylsilyl)-4-pentynoate, mono p-toluenesulfonic acid salt, treating the resulting salt with ethanol in the presence of p-toluenesulfonic acid, followed by neutralization to give (±)ethyl 3-amino-5-(trimethylsilyl)-4-pentynoate;

(d) treating (±)ethyl 3-amino-5-(trimethylsilyl)-4-pentynoate, the product of step c, with a catalytic amount of base in the presence of an alkanol solvent followed by a catalytic amount of acid to give the desilylated (±)ethyl 3-amino-4-pentynoate in situ, treating (±)ethyl 3-amino-4-pentynoate with (R)-(−)-mandelic acid in the presence of aprotic solvents to give ethyl 3S-amino-4-pentynoate compounded with αR-hydroxybenzeneacetic acid;

(e) treating 4-aminobenzamidine dihydrochloride with succinic anhydride and pyridine in the presence of an aprotic solvent to give 4-[[4-(aminoiminomethyl)phenyl]amino]- 4-oxobutanoic acid, monohydrochloride;

(f) treating ethyl 3S-amino-4-pentynoate compounded with αR-hydroxybenzeneacetic acid, the product of step d, with gaseous hydrochloric acid in the presence of an aprotic solvent to give ethyl 3S-amino-4-pentynoate, monohydrochloride; and (g) treating 4-[[4-(aminoiminomethyl)phenyl]amino]-4-oxobutanoic acid, monohydrochloride, the product of step e, with isobutyl chloroformate and N-methylmorpholine in the presence of an aprotic solvent followed by ethyl 3S-amino-4-pentynoate, monohydrochloride, the product of step f, with N-methylmorpholine to give ethyl 3S-[[4-[[4-(aminoiminomethyl)phenyl]amino]-1,4-dioxobutyl]amino]- 4-pentynoate, monohydrochloride with the understanding that when a pharmaceutically acceptable acid addition salt other than hydrochloride is desired the ethyl 3S-amino-4-pentynoate compounded with αR-hydroxybenzeneacetic acid, the product of step d, is treated with the appropriate acid corresponding to the desired salt and with the further understanding that the final salt of step e is identical to the final salt of step f.

* * * * *